United States Patent [19]

VandenBerg

[11] Patent Number: Plant 6,881

[45] Date of Patent: Jun. 27, 1989

[54] CHRYSANTHEMUM PLANT NAMED FINA

[75] Inventor: Cornelius P. VandenBerg, Salinas, Calif.

[73] Assignee: Yoder Brothers, Inc., Barberton, Ohio

[21] Appl. No.: 173,082

[22] Filed: Mar. 25, 1988

[51] Int. Cl.[4] ..... A01H 5/00

[52] U.S. Cl. ..... Plt./74

[58] Field of Search ..... Plt./74

*Primary Examiner*—Robert E. Bagwill

*Attorney, Agent, or Firm*—Foley & Lardner, Schwartz, Jeffery, Schwaab, Mack, Blumenthal & Evans

[57] ABSTRACT

A Chrysanthemum plant named Fina particularly characterized by its flat capitulum form; anemone capitulum type; white ray floret color; diameter across face of capitulum of up to 10 cm at maturity, with diameter of anemone cushion up to 2 cm; uniform eight week photoperiodic flowering response to short days; peduncle length ranging from 8 to 20 cm on open, terminal sprays; medium plant height when grown as a single stem spray cut mum; and excellent tolerance to low temperatures for bud initiation and flower development.

3 Drawing Sheets

The present invention comprises a new and distinct cultivar of Chrysanthemum, botanically known as *Dendranthema grandiflora,* and referred to by the cultivar name Fina.

Fina, identified as 84567006, was originated from a cross made by Cornelis P. VandenBerg in a controlled breeding program in Salinas, Calif. in 1984.

The female parent and the male parent of Fina were both unnamed seedlings, identified respectively as 79I70026 and 78e24002.

Fina was discovered and selected as one flowering plant within the progeny of the stated cross by Cornelis P. VandenBerg in May 1985 in a controlled environment in Salinas, Calif.

The first act of asexual reproduction of Fina was accomplished when vegetative cuttings were taken from the initial selection in July 1985 in a controlled environment in Salinas, Calif., by technicians working under formulations established and supervised by Cornelis P. VandenBerg.

Horticultural examination of controlled flowerings of successive plantings has shown that the unique combination of characteristics as herein disclosed for Fina are firmly fixed and are retained through successive generations of asexual reproduction.

Fina has not been observed under all possible environmental conditions. The phenotype may vary significantly with variations in environment such as temperature, light intensity, and daylength.

The following observations, measurements and comparisons describe plants grown in Salinas, Calif. under greenhouse conditions which approximate those generally used in commercial greenhouse practice. The low temperature tolerance was determined in repeated flowerings in Bogota, Columbia.

The following traits have been repeatedly observed and are determined to be basic characteristics of Fina, which, in combination, distinguish this Chrysanthemum as a new and distinct cultivar:

1. Flat capitulum form.
2. Anemone capitulum type.
3. White ray floret color.

4. Diameter across face of capitulum up to 10 cm at maturity, with diameter of anemone cushion up to 2 cm.
5. Uniform eight week photoperiodic flowering response to short days.
6. Peduncle length ranging from 8 to 20 cm on open terminal sprays.
7. Medium plant height, requiring two long day weeks prior to short days to attain a flowered plant height of 90 to 100 cm for year-round flowerings.
8. Excellent tolerance to low temperatures for bud initiation and flower development.

The accompanying photographic drawings show typical inflorescence and leaf characteristics of Fina, with the colors being as nearly true as possible with illustrations of this type.

Sheet 1 is a color photograph of Fina grown as a single stem cut spray mum.

Sheet 2 is a black and white photograph of three views of the inflorescence of Fina.

Sheet 3 is a black and white photograph showing the upper and under sides of the leaves of fina at three stages of development (mature, intermediate and immature).

Of the commercial cultivars known to the inventor, the most similar in comparison to Fina is White Marble. Reference is made to Chart A, which compares certain characteristics of Fina to the same characteristics of White Marble.

Similar traits are ray floret color, plant height and low temperature tolerance. The capitulum type of Fina is anemone, that of White Marble is a daisy. The peduncle length of Fina is shorter, the diameter of capitulum is larger and the flowering response is less than White Marble. Under adverse conditions White Marble exhibits compounding of the spray formation and develops bract tissue in the disc. The spray formation of Fina is always terminal, with no development of bracts.

In the following description, color references are made to The Royal Horticultural Society Colour Chart. The clear white ray floret color of Fina is not represented in The Royal Horticultural Society Colour Chart. The color values were determined on plant material grown in Salinas, Calif. on Oct. 8. 1987.

Classification:

*Botanical.*—*Dendranthema grandiflora,* cv Fina.

*Commercial.*—Anemone cut spray mum.

INFLORESCENCE

A. Capitulum:

*Form.*—Flat.

*Type.*—Anemone.

*Diameter across face.*—Up to 10 cm at maturity.

*Diameter of anemone cushion.*—Up to 2 cm.

B. Corolla of ray florets:

*Color (general tonality from a distance of three meters).*—White.

*Color (upper surface).*—White.

*Color (under surface).*—White.

*Shape.*—Flat, oblong.

C. Corolla of disc florets:

*Color (mature).*—Closest to 154B.

*Color (immature).*—Closest to 143B.

D. Reproductive organs:

*Androecium.*—Present on disc florets only; scant pollen.

*Gynoecium.*—Present on both ray and disc florets.

PLANT

A. General appearance:

*Height.*—Medium, 90 to 100 cm as a single stem cut mum with 2 long day weeks prior to short days.

B. Foliage:

*Color (upper surface).*—147A.

*Color (under surface).*—147B.

*Shape.*—Lobed and slightly serrated.

CHART A

COMPARISON OF FINA AND WHITE MARBLE

| | Fina | White Marble |
|---|---|---|
| Ray floret color | White | White |
| Capitulum form and type | Flat Anemone | Flat Daisy |
| Spray formation | Terminal 8 to 20 cm peduncles | Terminal to compound 20 to 25 cm peduncles |
| Diameter across face of capitulum | Up to 10 cm | Up to 9 cm |
| Plant height | Medium | Medium |
| Flowering response period | 8 weeks | 9 weeks |
| Low temperature tolerance | Excellent | Good |

COMPARISONS MADE OF PLANTS GROWN AS SINGLE STEM SPRAY CUT MUMS IN SALINAS, CALIFORNIA

I claim:

1. A new and distinct Chrysanthemum plant named Fina, as described and illustrated, and parts thereof.

* * * * *

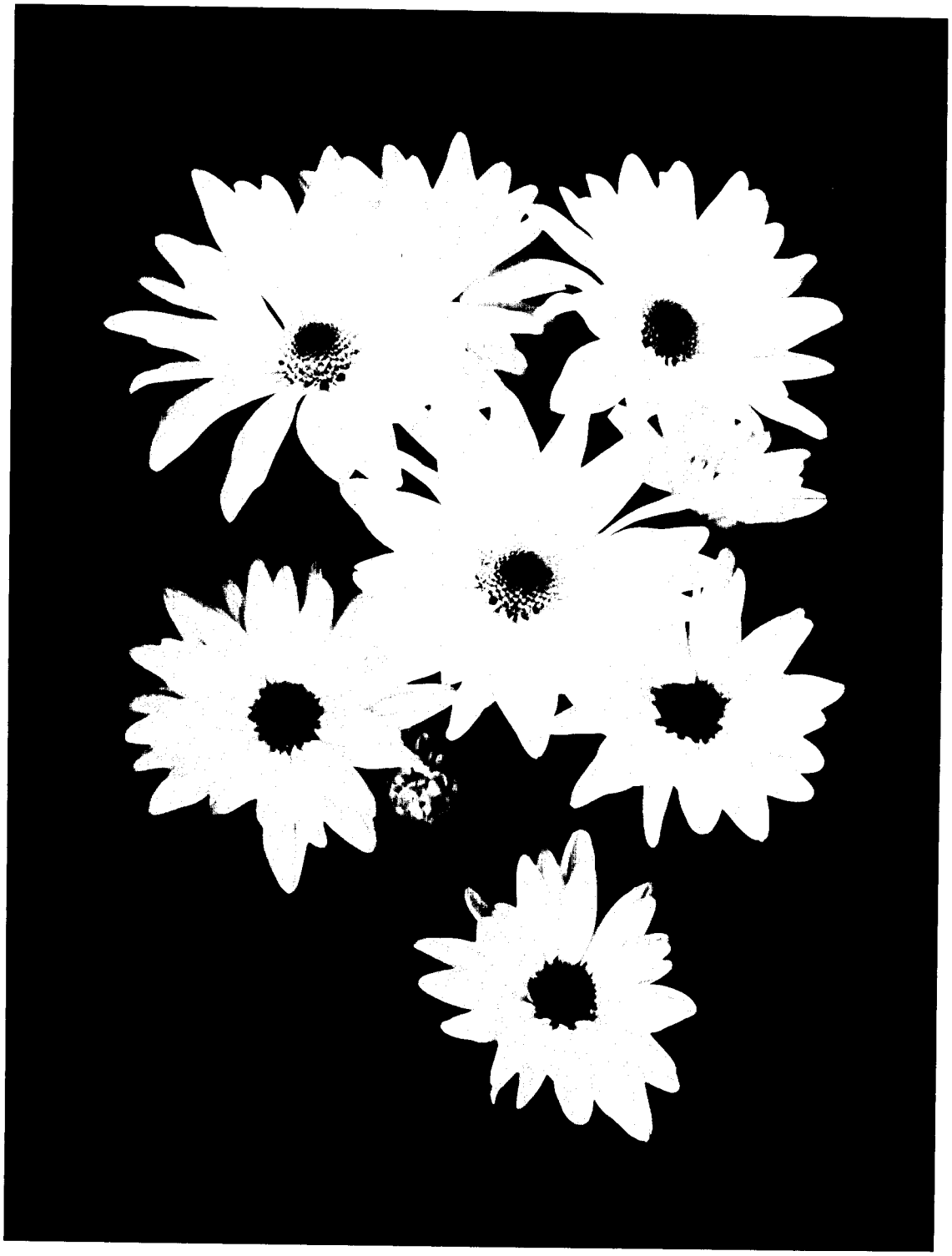

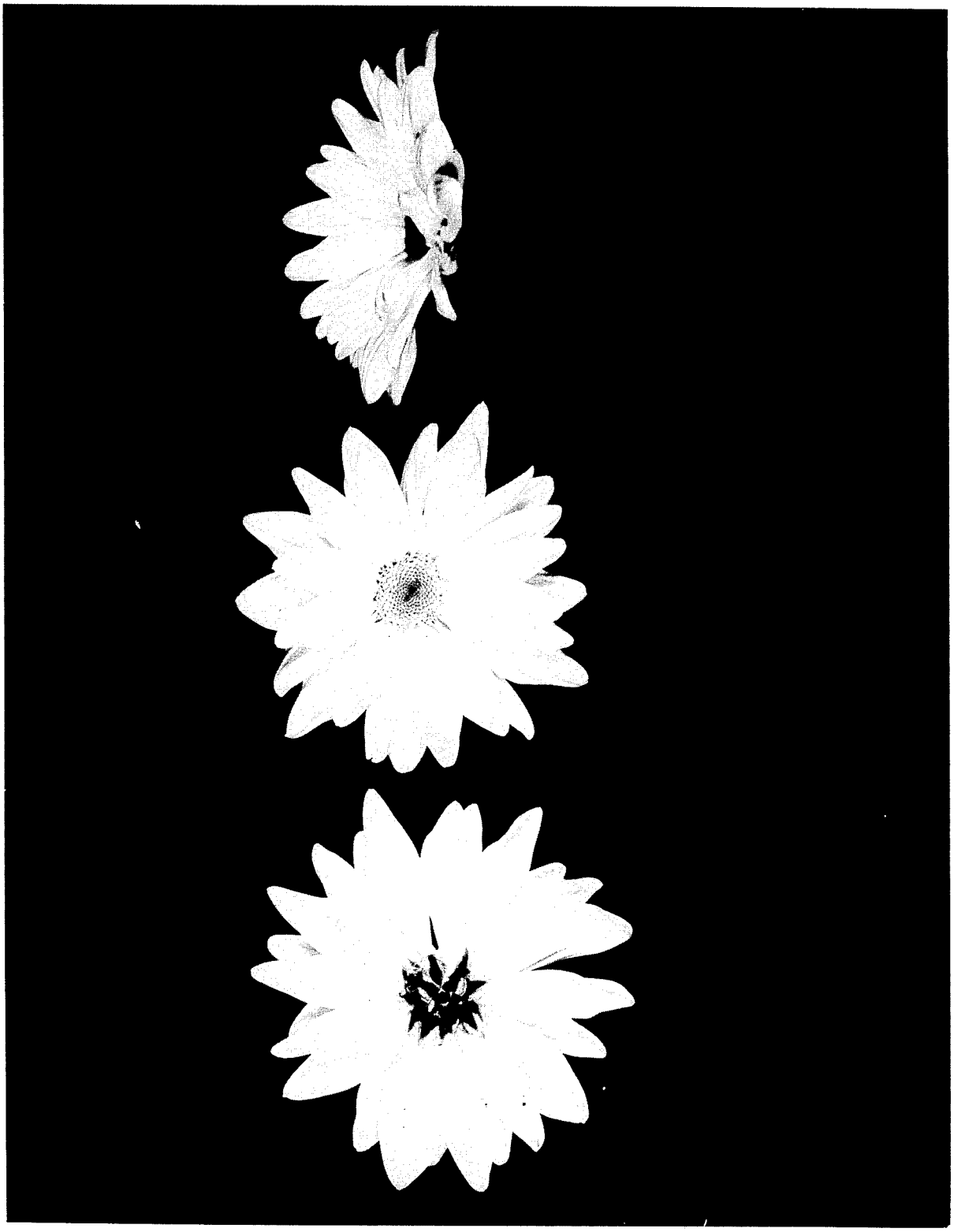

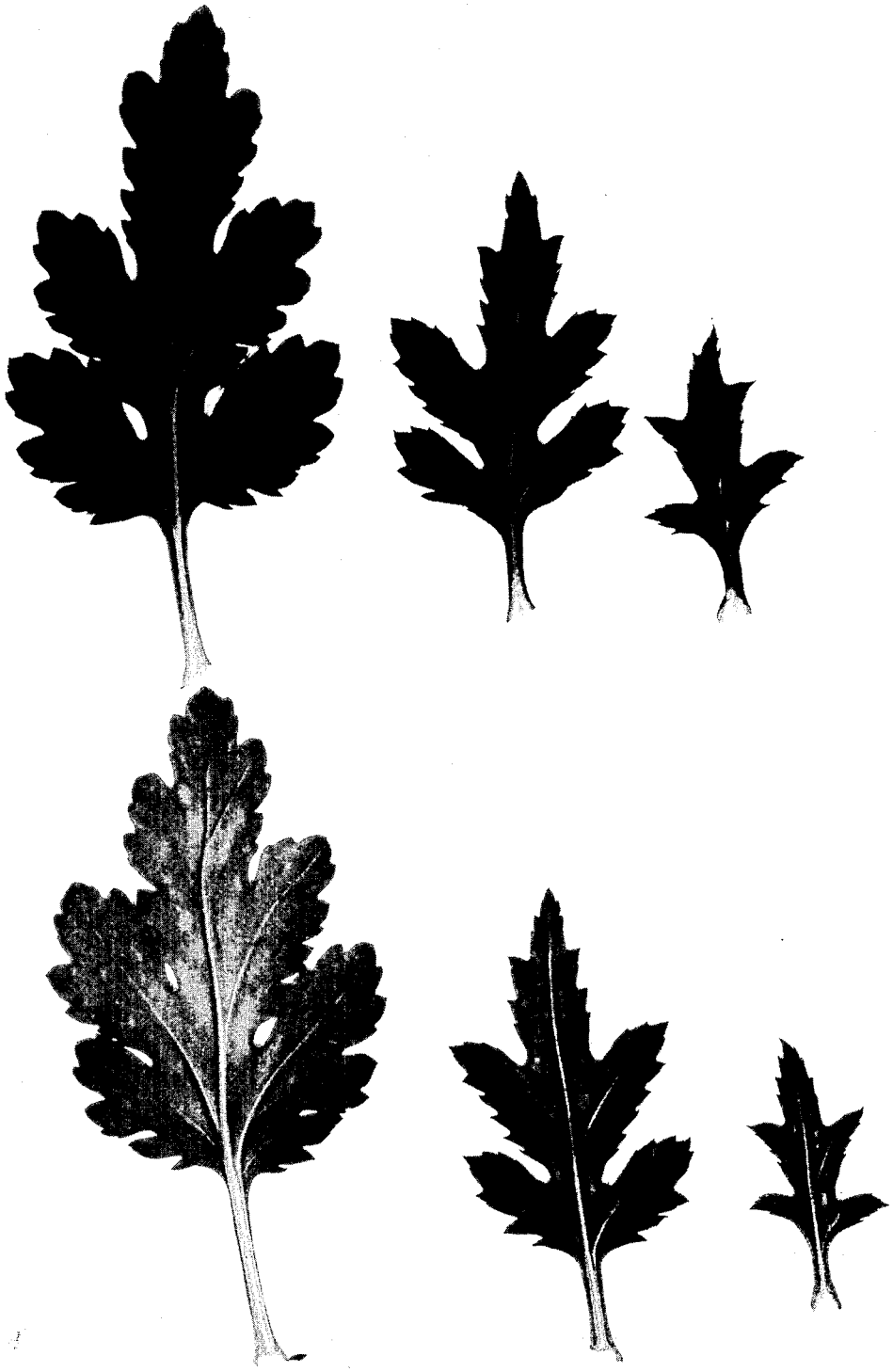

UNITED STATES PATENT AND TRADEMARK OFFICE

CERTIFICATE OF CORRECTION

PATENT NO. : PP 6,881

DATED : June 27, 1989

INVENTOR(S) : Cornelis P. VandenBerg

It is certified that error appears in the above—identified patent and that said Letters Patent is hereby corrected as shown below:

Column 1, Line 10, "78e24002" should be "78@24002".

Column 1, Line 35, "Columbia" should be "Colombia".

Column 2, Line 22, "fina" should be "Fina".

Signed and Sealed this

Twenty-sixth Day of June, 1990

*Attest:*

HARRY F. MANBECK, JR.

*Attesting Officer*

*Commissioner of Patents and Trademarks*